United States Patent [19]

Sweeney et al.

[11] Patent Number: 4,628,942

[45] Date of Patent: Dec. 16, 1986

[54] ASYMMETRIC SHIELDED TWO ELECTRODE CUFF

[75] Inventors: James D. Sweeney; J. Thomas Mortimer, both of Cleveland Heights, Ohio

[73] Assignee: Case Western Reserve University, Cleveland, Ohio

[21] Appl. No.: 659,823

[22] Filed: Oct. 11, 1984

[51] Int. Cl.⁴ .............................................. A61N 1/04
[52] U.S. Cl. ..................................... 128/784; 128/422
[58] Field of Search ................................ 128/784–785, 128/642, 419 C, 802

[56] References Cited

U.S. PATENT DOCUMENTS

Re. 26,810  3/1970  Schwartz et al. .............. 128/784
3,157,181  11/1964  McCarty ......................... 128/784
3,654,933  4/1972  Hagfors .......................... 128/784
3,738,368  6/1973  Avery et al. .................... 128/784
3,774,618  11/1973  Avery ............................. 128/784
4,341,221  7/1982  Testerman ...................... 128/642

OTHER PUBLICATIONS

"A Technique for Collision Block of Peripheral Nerve: Single Stimulus Analysis", IEEE Trans. on Biomed. Eng., vol. BME-28, No. 5, May 1981.
"A Technique for Collision Block of Peripheral Nerve: Frequency Dependence", IEEE Trans. on Biomed. Engr., vol. BME-28, No. 5, May 1981.
"Generation of Unidirectionally Propagated Action Potentials in a Peripheral Nerve by Brief Stimuli", Science, vol. 206, pp. 1311-1312, Dec. 1979.

Primary Examiner—William E. Kamm
Assistant Examiner—Mitchell J. Shein
Attorney, Agent, or Firm—Fay, Sharpe, Fagan, Minnich & McKee

[57] ABSTRACT

A nerve trunk (A) has an annular electrode cuff (B) positioned therearound for imposing electrical signals on to the nerve trunk for the purpose of generating unidirectionally propagated action potentials. The electrode cuff includes an annular cathode (30) having a circular passage therethrough of a first diameter. An annular anode (40) has a larger circular passage therethrough of a second diameter, which second diameter is about 1.2 to 3.0 times the first diameter. A non-conductive sheath (50) extends around the anode, cathode, and nerve trunk. The anode and cathode are placed asymmetrically to one side of the non-conductive sheath. Specifically, a first length (L1) along the electrode sheath between a first end (56) and the cathode is at least twice a second length (L2) between the anode and cathode. A third length (L3) between the anode and a second end (58) of the conductive sheath is smaller than the first or second lengths. With this geometry, the majority of the current applied to the anode electrode flows to the cathode along path segments (62b and 62d) with lesser amounts of current flowing in the path segments (64a), (64b), (66a), and (66b).

2 Claims, 4 Drawing Figures

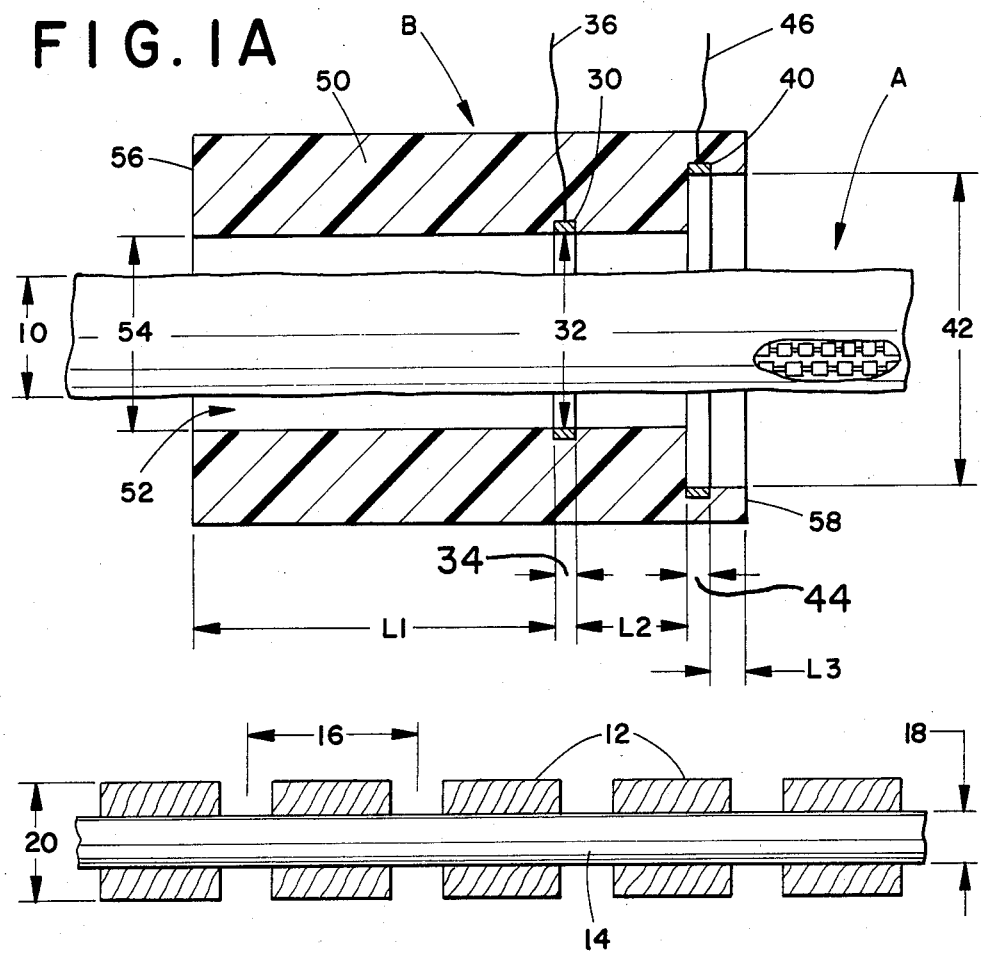
FIG. 1A
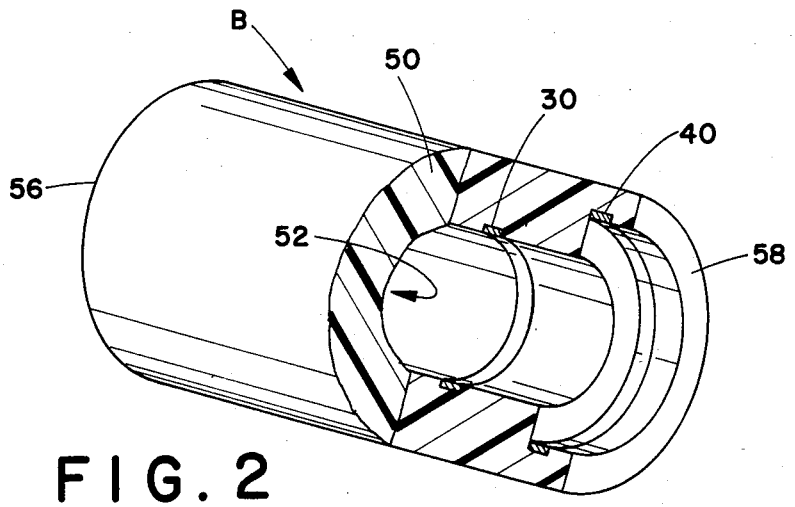
FIG. 1B
FIG. 2

ASYMMETRIC SHIELDED TWO ELECTRODE CUFF

BACKGROUND OF THE INVENTION

The present invention relates to biomedical electrodes. It finds particular application in electrodes for surrounding a nerve trunk to introduce electrical stimuli thereon for the purpose of generating action potentials that propagate in only one direction from the cuff. It is to be appreciated, however, that the present invention may find other utility.

Heretofore, others have used electrical stimuli to create action potentials that in turn cause the release of a neurotransmitter that may result in a measurable physiological response. Many of these prior art stimulation techniques applied the electrical stimuli to peripheral nerves subserving muscle or peripheral sense organs, bypassing the higher levels of the nervous system. It has also been found that electrical signals can be applied to other excitable tissue directly, such as muscle. Although the applied electrical signals can cause the nervous system to activate appropriate muscles or other organ responses, another potentially important use is to block the naturally generated action potentials traveling along a nerve fiber.

Specifically, the proper application of electrical signals can block nerve impulses traveling up the nerve trunk toward the brain to arrest pain signals, phantom limb signals in amputees, and the like. Analogously, appropriately generated action potentials can block nerve impulses traveling on the nerve trunk to eliminate nerve impulses which cause unwanted physiological activity. For examle, the stimuli can block signals which cause spasmodic behavior, hiccups, and the like. A potential application is to cause the controlled relaxation of the external urinary bladder or sphincter in paralyzed patients who have lost this control. With proper application of electrical signals, a paraplegic with a loss of voluntary bladder control can void the contents of the bladder.

Various electrical potentials have been applied between a cathode and an anode to suppress the transmission of unwanted nerve action potentials. Some researches have used DC currents flowing from the anode to the cathode to block natural nerve impulses. Others have used high frequency sinusoidal stimulation to block natural nerve impulses.

In the past, electrical stimuli have been applied to the nerves for the purpose of generating unidirectional propagating action potentials with cuffs containing three electrodes. The prior art electrode cuff included a dielectric, i.e., electrically non-conductive, cylindrical tube or sleeve. Three annular electrodes were disposed along the inner surface of the sleeve. That is, a cathode electrode was commonly positioned centrally in the sleeve and a pair of anode electrodes were positioned to either side thereof and displaced from the ends of the sleeve.

The electrodes have been utilized to introduce a string of artificially generated antidromic pulses which propagate unidirectionally in the opposite direction to the normal orthodromic pulse flow. The antidromic pulses collide with the natural orthodromic nerve impulses coming the other direction, blocking them from further propagation. An exemplary antidromic pulse generating electrical signal is a series of pulses each of which has a vertical leading edge, a period of constant amplitude followed by an exponentially decaying trailing edge.

Once inserted in the body, the three electrode cuff was immersed in electrically conductive body fluids and tissues. Electric currents were selectively caused to flow from both of the anodes by separate sources, through the conductive body fluids and tissues, through the nerve trunk to the centrally disposed cathode. The like diameter anodes and cathode were disposed along and within an insulating sleeve. In this manner, substantially all current flowed from the anodes to the cathode through the interior of the sleeve with little current flow around the exterior of the sleeve. The one anode at the escape end acts to suppress a secondary current path from the other anode, flowing out the insulating sleeve at the arrest end and entering the cuff from the escape end. This secondary current, which passed through the nerve, if not suppressed, can cause action potentials to be generated at a site away from the arrest end of the cuff by virtue of the direction of its flow. The current flowing from the anode, positioned at the escape end, is controlled by a current source that is separate from the one supplying the anode at the arrest end. The magnitude of the current flowing at the escape anode must be such that it will only suppress the secondary current flow arising from the arrrest end anode and not itself cause arrest of the approaching antidromic action potential.

The second current source would tend to create a number of problems with the prior art cuff electrodes. First, excess electrode current must be carried by the shared cathode. The excess current is that component applied for the purpose of suppressing the secondary current arising from the arrest end anode. This extra current could be injurious or cause the cathode to be unnecessarily large compared to the nerve. Further, the requirement for two separate current sources that are synchronously activated adds significant complexity to a cuff as opposed to using only a single current source.

The present invention contemplates a new and improved electrode cuff which eliminates (1) the second anode at the escape end, (2) the requirement for a second current source and (3) the high charge or current density at the cathode, yet overcomes the above-referenced problems and others.

SUMMARY OF THE INVNETION

In accordance with the present invention, an electrode cuff is provided for introducing electrical signals or action potentials on a nerve trunk. An insulating shield extends a first length from a first end to a generally annular cathode, a second length from the cathode to a generally annular anode, and a third length from the anode to a second end. The first length between the first end and the cathode is at least twice the second length between the cathode and anode. The third length between the anode and the second end is less than the first and second lengths. This asymmetric positioning of the electrodes relative to the insulating shield significantly limits current flow around the exterior of the cuff.

In accordance with another aspect of the invention, the cathode and anode are circular rings such that the cross section of each is defined by its diameter. The anode diameter is greater, preferably 1.2 to 3.0 times greater, than the cathode diameter.

A primary advantage of the present invention is that it reduces current flow through body tissue around the cuff exterior and maximizes primary current flow through the nerve trunk.

Another advantage resides in a reduced risk of nerve damage.

Yet another advantage is improved performance and reliability. Only one stimulator current source is required.

Still other advantages of the present invention will become apparent to those of ordinary skill in the art upon reading and understanding the following detailed description of the preferred embodiment.

BRIEF DESCRIPTION OF THE DRAWINGS

The present invention may take form in various parts and arrangements of parts. The drawings are only for purposes of illustrating a preferred embodiment of the invention and are not to be construed as limiting it.

FIG. 1A is a side sectional view of an asymmetric two-electrode cuff in accordance with the present invention with a nerve trunk passing therethrough;

FIG. 1B is an enlarged view of a single myelinated axon of the nerve trunk of FIG. 1A.

FIG. 2 is a perspective view of the cuff of FIG. 1A; and,

DETAILED DESCRIPTION OF THE PREFERRED EMBODIMENT

Figure 3:
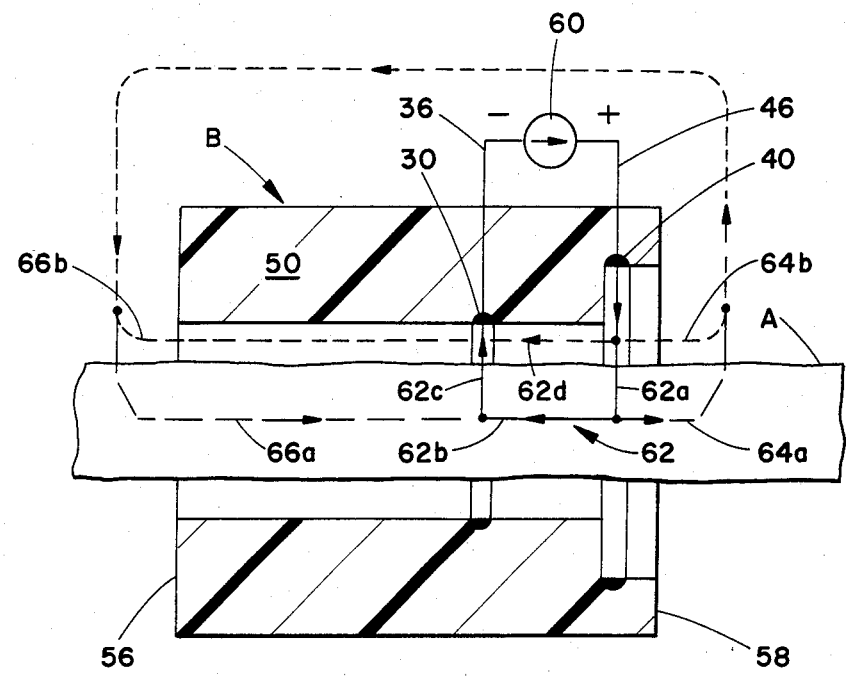
FIG. 3 is a side sectional view of the cuff of FIG. 1A illustrating the application of electrical potentials to the electrodes thereof.

With reference to FIG. 1A, a nerve trunk A is threaded loosely through an electrode cuff B. With time, electrically conductive body tissue and fluids, not shown, fill the gap between the nerve trunk and the cuff.

The nerve trunk A is a large bundle of nerves or axons which taken together have a major diameter 10. As illustrated in FIG. 1B, each axon includes a plurality of myelin sheaths 12 disposed at regular axial intervals along an axoplasm containing axon membrane 14 with nodes of Ranvier at openings between the myelin sheaths. Extracellular fluid, not shown, is disposed around the myelin sheaths and the axom membrane to bathe and nourish the axons. Each axom has a characteristic internodal length 16 which is characteristic of the spacing of the myelin sheaths and Ranvier nodes. The axons can further be characterized by an axoplasm diameter 18 and a myelin sheath or nerve fiber diameter 20. It is to be appreciated that the FIG. 1B axon is out of proportion to simplify illustration. Commonly, the internodal length 16 is about 100 times the nerve fiber diameter 20. Although described with reference to myelinated fibers, it is to be appreciated that the present invention is also applicable to unmyelinated nerve fibers.

With continuing reference to FIG. 1A and further reference to FIG. 2, the cuff B includes an annular first electrode or cathode 30 which defines a passage with a first cross section therethrough. In the preferred embodiment, the cathode is a circular ring and the passage therethrough is defined by a cathode diameter 32. The cathode has an exposed cathode width 34 measured axially along the cuff. A cathode lead wire 36 extends from the cathode for interconnection with associated circuitry.

The cuff further includes an anode or second electrode 40. The anode is again annular, preferably circular, to define a second cross section therethrough which is characterized by a second or anode diameter 42. The anode has a longitudinal width 44. An anode lead wire 46 extends from the anode to appropriate electrical signal applying circuitry. In the preferred embodiment, the anode diameter is 1.2 to 3.0 times the cathode diameter, i.e., the anode cross section is 1.4 to 9 times the cathode cross sectional area.

A dielectric, electrically non-conductive sheath or shield 50 extends around the anode and cathode electrodes, as well as the nerve trunk A. The non-conductive sheath defines a nerve trunk receiving passage 52 therethrough which is substantially the same major diameter 54 as the cathode diameter. Optionally, the cathode may project from the surface of the non-conducting sheath inner bore such that the shield inner bore is slightly larger in daimeter than the cathode. Alternately, the cathode may be greater in diameter than the shield internal bore and recessed below the inner surface of the bore. The non-conductive sheath defines a first or escape end 56 disposed a first length L1 from the cathode. The cathode, in turn, is mounted to the non-conducting sleeve a second length L2 from the anode. The anode, in turn, is disposed a third length L3 from a second or arrest end 58.

With reference to FIG. 3, the application of an electrical potential from an electrical stimulator source 60 causes a primary stimulus current to flow along path 62, more particularly, along path segments 62a, 62b, 62c, and 62d. The current flowing transverse to the nerve membrane at the site under the cathode and in the direction of current 62c gives rise to the generation of action potentials that propagate toward each end of the cuff. Current flowing through the nerve membrane under the anode and in the direction 62a will be opposite to that required to depolarize the nerve membrane. If this current is of sufficient magnitude and applied for sufficient time it can block the depolarizing effects of currents arising from the approaching action potential, arresting any further propagation of the action potential. Current arising from the anode and flowing across the nerve membrane 62a can take two pathways to the cathode 30, either pathway 64a or pathway 62b. Current taking pathway 64a will exit the nerve membrane at a point outside the arrest end of the cuff 58. The direction of this current is such that it can depolarize the nerve membrane and give rise to a propagated action potential at this site if the magnitude of this current is of a sufficient strength. The tendency for action potential generation at this site external to the arrest end of the cuff can be reduced by decreasing the magnitude of the current flowing along this pathway. The magnitude of the current flowing along pathway 64a can be reduced by increasing the resistance along pathway 66a and 66b compared to pathway 62b. The larger the length L1 compared to length L2 the lower the current along pathways 66a and 66b compared to pathway 62b.

The generating or blocking of nerve pulses or action potentials is determined by the nature of the electric wave applied and is well known in the art. In the preferred embodiment, the stimulator source generates a repetitive electric signal in which each cycle includes a rapidly rising leading edge, a pulse width or plateau with a several milliampere amplitude, i.e., a rectangular wave, and an exponential decay portion with a 90%-10% fall time. Preferably, the signal is biphasic and includes an opposite polarity lower amplitude secondary pulse after each primary pulse.

The present asymmetric arrangement minimizes the secondary current flow along segments 64a and 66a to improve electrode cuff performance. The cathode and anode are located asymmetrically relative to the ends of non-conducting sheath 50, with the first length distance L1 greater than the second length L2. Specifically, the first length L1 is at least twice and preferably less than 4 times the second length L2. In the preferred embodiment, the first length is 2.5 times the second length. The second length is selected such that the primary current 62b flows over at least 2 nodes of Ranvier of the largest diameter axon in the nerve trunk. The second length is selected to be at least twice and preferably 3 to 5 times the internodal length of the largest axons 16. In the preferred embodiment the second length is between 3 and 4 times the internodal length. The third length L3 which is relatively short to maximize performance is less than 4 times the maximum internodal length 16. In the preferred embodiment, the third length is 2 times the internodal length, although satisfactory values are achieved with the third length three times the internodal length. Further, the third length L3 is sufficiently short that the first length L1 extends over half the total length of the non-conducting sleeve.

Further, the anode major diameter 32 is larger than the cathode diameter 42, preferably with a ratio of 1.2 to 3.0. An anode diameter to cathode diameter ratio of 1.33 yields excellent performance.

The cathode diameter should be about 1.30 to 2.0 times the major diameter of the nerve trunk. The cathode should have a sufficiently large diameter that the nerve trunk fits therethrough without being compressed. Yet, the cathode diameter should be sufficiently small that good electrical conduction is provided therebetween. When the nerve trunk is generally circular in diameter, a cathode diameter of 1.3 to 1.4 times the nerve trunk diameter produces excellent results. For elliptically shaped nerve trunks, the cathode diameter may be as great as twice the diameter of the nerve trunk. Alternately, the cathode may be ellipitical with its major and minor axes being about 1.3 to 1.4 times the major and minor axes, respectively, of the nerve trunk.

Although exact physical dimensions may vary with the nerve trunk which is to pass through the cuff, satisfactory physical dimensions are as follows: the anode width 34 and the cathode width 44 each equal to 1 mm; the first length L1 equal to 16 mm; the second length L2 equal to 6 mm; the third length L3 equal to 4 mm; the cathode diameter 42 equal to 4.2 mm; and, the anode diameter 32 equal to 5.6 mm, given a nerve diameter of 3 mm.

The invention has been described with reference to the preferred embodiments. Obviously, modifications and alterations will occur to others upon reading and understanding the preceding detailed description of the preferred embodiments. It is intended that the invention be construed as including all such alterations and modifications insofar as they come within the scope of the appended claims or the equivalents thereof.

Having thus described the preferred embodiment of the invention, the invention is now claimed to be:

1. An electrode cuff for introducing unidirectionally propagated action potentials in a single direction on a nerve trunk, the cuff comprising:
    a generally annular cathode defining a first passage therethrough of a first diameter;
    a generally annular anode defining a second passage therethrough of a second diameter, the second diameter being 1.2 to 3.0 times as large as the first diameter such that the cathode is more proximate to the nerve trunk passing therethrough than the anode; and,
    an insulating shield extending from a first end thereof to the cathode, from the cathode to the anode, and from the anode to a second end thereof, a distance between the cathode and the first end being at least twice a distance between the cathode and the anode.

2. A nerve stimulator system for inducing unidirectionally propagating action potentials on a nerve trunk, the system comprising:
    a two electrode cuff including: a first annular electrode defining a first passage therethrough having a first diameter that is larger than the trunk diameter, a second annular electrode defining a second passage therethrough having a second diameter which is larger than the first diameter, an insulating electrical shield extending around the nerve trunk and the first and second electrodes, the insulating shield having a first length extending from a first end thereof to the first electrode, a second length between the first and second electrodes and a third length extending from the second electrode to a second end thereof, the first length being at least two times the combined second and third lengths such that the second electrode is closer to the second end than the first electrode is to the first end; and,
    a signal generator for applying an oscillatory signal to the first and second electrodes such that the first electrode is primarily biased as a cathode and the second electrode is primarily biased as an anode.

* * * * *